United States Patent [19]

Beise et al.

[11] 4,145,192

[45] Mar. 20, 1979

[54] METHOD OF PROCESSING TECHNICAL GASES

[76] Inventors: Hans Beise, Schieritzstr. 19; Burkhard Schlicht, Lehnestr. 31; Manfred Thiele, Schlossalle 29 a, all of Berlin; Manfred Gross, Strasse d. Einheit 17, Freiberg, Sa; Hans-Peter Minak, Am seilerberg 23, Freiberg, Sa; Manfred Schingnitz, Kornerstr. 19, Freiberg, Sa; Klaus Wehner, Hocker Gasse 1, Leuna; Werner Burk, Block 247, Haus 10, Halle-Neustadt, all of German Democratic Rep.

[21] Appl. No.: 771,147

[22] Filed: Feb. 23, 1977

[30] Foreign Application Priority Data

Feb. 23, 1976 [DD] German Democratic Rep. ... 191435

[51] Int. Cl.$^2$ ............................................. B01D 53/02
[52] U.S. Cl. ........................................... 55/32; 55/73; 55/84; 423/226; 252/194

[58] Field of Search ....................................... 55/29–32, 55/46–51, 68, 173, 84; 423/226; 252/364, 194

[56] References Cited

U.S. PATENT DOCUMENTS

| 3,471,370 | 10/1969 | Jubin, Jr. | 55/32 |
|---|---|---|---|
| 3,653,809 | 4/1972 | Wehner et al. | 55/68 |
| 3,745,746 | 7/1973 | Psyras et al. | 55/31 |
| 3,968,104 | 7/1976 | Wagner | 252/364 |

*Primary Examiner*—Bernard Nozick
*Attorney, Agent, or Firm*—Nolte & Nolte

[57] ABSTRACT

A method of processing technical gases such as natural or synthetic gases containing water vapor, acidic and neutral sulfur compounds and/or higher hydrocarbons which comprises treating said gas with an anhydrous solvent containing N-methyl-ε-caprolactam, an alkanolamine and a glycol to simultaneously remove said sulfur compounds, hydrocarbons and water vapor.

6 Claims, No Drawings

METHOD OF PROCESSING TECHNICAL GASES

FIELD OF THE INVENTION

This invention relates to a method of simultaneously purifying and drying technical gases such as natural or synthetic gas by means of a non-aqueous solvent.

DISCUSSION OF THE PRIOR ART

One of the best known methods for removing acid components (primarily $H_2S$ and $CO_2$) from technical gases is the alkanolamine method, whereby mono-, di-, or tri-ethanolamine is used singly or in admixture in a hydrous solution as the solvent. (H. Franik; Earth gas processing, page 30; VEB Deutscher Verlag fur Grundstoffindustrie, Leipzig, 1964).

It is also known to use mixtures of alkanolamines, glycols and water for removing acidic sulphur containing compounds (Ullmann; Encyclopedia of technical chemistry, Vol. 6, pages 740 etc. 3rd edition), wherein the solvent mixture comprises 10 to 30 percent by weight mono-, di-, or tri-ethanolamine, 45 to 85% by weight diethyleneglycol and 5 to 25% by weight water (H. Franik; Earth gas processing, page 38).

This solvent mixture makes it possible to simultaneously remove a small amount of water in addition to the hydrogen sulfide and the carbon-dioxide.

Another known method for removing acid gas components from technical gases, is the sulfinol method, which combines solvent components having physical and chemical effects. The solvent used here is a hydrous solution of alkanolamines and tetrahydrothiophene 1,1 dioxide. (W. G. I. van Dajk, J. G. Tonis, "Das Shell-Sulfinol Verfahren"; Erdol und Kohle, Erdgas, Petrochemie 19 (1966) 6, Pgs. 404–406). This solvent composition comprises a mixture of 45 to 65 percent by weight diisopropanol amine, 20 to 40% by weight tetrahydrothiophene 1,1 dioxide (sulfolan) and 10 to 40% by weight water (German Published Application No. 1,769,340).

There are also known methods wherein hydrous solutions of mono- and di-ethanolamine as well as sulfolan are being utilized (German Published Application No. 1,544,122).

Still another known method uses as the solvent for removing acid gas components, N-substituted ε-caprolactam (DL-WP 83 630). This method is used primarily when $CO_2$, $H_2S$ and mercaptans have to be removed. In accordance with this method, mixtures of methyl-ε-caprolactam and hydrous alkanolamines are utilized.

THE DISADVANTAGE OF THESE PRIOR ART METHODS

There are many disadvantages in the use of the aforementioned solvents in the processing of technical gases at normal temperatures. One essential problem is that although the acid components such as the $CO_2$ & $H_2S$ are removed, the water vapor dew point is not concurrently reduced, thereby requiring a subsequent drying step. This is especially true of the ethanolamine method, the sulfinol method and the N-methyl-ε-caprolactam method. Another essential problem, especially inherent in the glycolamine method, is that the solvent does not remove the acidic organic sulfur compounds to a sufficient degree, thereby necessitating an additional purification step.

Characteristic of the prior art methods is the use of aqueous solvents, when alkanolamines are present in the solvent mixture. The absence of water in these mixtures leads to a considerable reduction in the degree of desulphuration. If, for example, the water content is reduced in the solvent mixture of monoethanolamine and water by the addition of from 5–83% diethyleneglycol, by weight, the degree of desulphuration for $H_2S$ decreases a minimum of ten percent (H. Franik, Earth gas processing, pgs. 35 and 39).

Another essential disadvantage of the prior art methods is the ineffectiveness of aforesaid solvents or solvent mixtures, in removing neutral organic sulphur compounds, such as thiophene, dimethylsulfide, and the like from natural gas.

Still another disadvantage of aforesaid methods which utilize alkanolamines or glycolamines in the solvent, is that the organic sulphur such as $CS_2$, COS, etc. form non-regenerating compounds with the former, which seriously hamper the effectiveness of these methods. Moreover, in accordance with aforesaid methods, the required degree of desulphuration is obtained only with the use of a large number of substance exchange units. This results in a costly operation.

In addition, the prior art solvents which contain glycols and/or alkanolamines, exhibit strong foaming tendencies in the presence of hydrocarbons, thereby requiring the use of foam-breakers such as amines, which further adds to the operational costs.

SUMMARY OF THE INVENTION

Accordingly, it has now been found that all of aforesaid disadvantages have been overcome by utilizing a non-aqueous solvent to treat technical gases.

More specifically, this invention relates to a method of processing technical gases, both natural and synthetic, containing water vapor, acid & neutral sulfur compounds and/or higher hydrocarbons, by contacting with an anhydrous solvent containing N-methyl-ε-caprolactam as the major constituent, preferable about 60–90%, about 5–60% of a glycol, and about 0–30% of an alkanolamine by weight.

This anhydrous solvent mixture possesses the unexpected property of providing a highly soluble medium for neutral and acidic organic sulfur compounds, as well as for aromatic and paraffinic hydrocarbons, thereby effecting their ready removal from the technical gases by means of the solvent. In addition to providing improved degrees of desulfuration and of purification, instant novel solvent effects the simultaneous drying of the gases by removing the water vapor therefrom. When the alkanolamine is included in the solvent mixture, no foaming is exhibited despite the normal tendency of alkanolamines to foam in the presence of hydrocarbons, emulsions and corrosion products.

Accordingly, it is an object of this invention to provide an improved method of processing technical gases which contain water vapor, acid and neutral sulfur compounds and/or higher hydrocarbons by means of an anhydrous solvent.

Another object of this invention is to provide a method for the simultaneous drying, desulfuration and purification of technical gases, with a uniform gas throughput.

Still another object of this invention is to provide a method for desulfurating substantially all sulfur compounds.

A further object of this invention is to provide a method whereby the charged solvent mixture can be substantially completely regenerated for reuse.

Still another object of the invention is to provide a method for processing technical gases which have a high water content, acid gas components, neutral organic sulphur compounds and higher hydrocarbons, in a manner whereby the drying and/or complete or selective removal of the neutral organic sulphur compounds, the acid gas components and the higher hydrocarbons can be carried out, at the same time.

In accordance with the invention, the solvent being used is a water-free mixture of N-methyl-ε-caprolactam, alkanolamine and glycol, wherein the glycol content is at least 5% by weight and up to 60% by weight, and the alkanolamine content is optional and amounts to a maximum of 30% by weight. The proposed anhydrous solvent mixture produces the surprising effect of a decidedly high solubility for neutral and acid organic sulphur compounds, as well as aromatic and higher paraffinic hydrocarbons, accompanied by a simultaneous drying effect. Particularly at the system pressures which are customary in the natural gas processing technique, the technical solubility coefficients of these solvent components are by 1 to $2^{10}$ points higher than for hydrogensulfide.

Another surprising effect is that the expected foam formation due to the alkanolamines contained in the instant solvent mixture, does not occur despite the presence of hydrocarbons, emulsions, and corrosion products.

Furthermore, the solvent mixture of this invention does not form compounds with the organic sulphur compounds, so that a complete regeneration of the solvent mixture is possible. If a particularly low vapor dew point is required, the method may be carried out in a manner wherein preferably di- or tri-ethylene glycol is used as the glycol. The solvent mixture of this invention can be used in all methods known in the prior art, with or without pressure.

The following examples are given to illustrate this invention further, and are not to be construed as limited thereto.

EXAMPLE 1

10,000 m³ i. N/h natural gas at a pressure of 60 atmospheres and a temperature of 20° C. are to be processed, so that the processed natural gas will contain <30 ppm of organic sulphur compounds, a vapor dew point of <−10° C. and a content of hydrocarbons >$C_7$ of <100 ppm. The crude gas is processed in a plate column with 25 plates, at a solvent cycle of 10 m³/h. The solvent comprises a mixture of 90% by weight N-methyl-ε-caprolactam and 10% by weight triethylene glycol. The purified gas has the following composition as compared to the crude gas:

|  | Crude Gas | Pure Gas |
|---|---|---|
|  | Volume % | Volume % |
| $CH_4$ | 91 | 93 |
| $C_2H_6$ | 5 | 4.6 |
| $C_3H_8$ | 2.4 | 1.6 |
| $C_4H_{10}$ | 1.3 | 0.5 |
| $C_5H_{12}$ | 0.3 | 0.1 |
|  | ppm | ppm |
| $C_6H_{14}$ | 450 | 160 |
| $C_7H_{16}$ | 270 | 90 |
| $CH_3$—$CH_2$—SH | 30 | 15 |
| $CH_3$—S—$CH_3$ | 70 | 7 |
| $CH_3$—SH | 180 | 4 |

|  | Crude Gas | Pure Gas |
|---|---|---|
| Hydrocarbons >$C_7$ | 100 ppm | 10 ppm |
| $H_2O$ - Dew point | 20° C | <−10° C |

Regeneration of the solvent is carried out in a column containing solid filler at a temperature of 160° C. Prior to heat regeneration, the charged solvent is relieved of stress in two stages (steps). During the first stage, the stress is relieved at a pressure of 20 atmospheres. This stress-relief gas is used as strip gas. The stress-relief gas of the second stage at 2 atmospheres, serves as heating gas for the process.

EXAMPLE 2

10,000 m³ i.N/h natural gas is treated at 50 atmospheres and 20° C. to remove the acid gas components and the organic sulphur compound down to a content of 25 ppm, said gas being simultaneously dried. The crude gas is processed in a solid filler-containing column, with a solvent cycle of 16 m³/h. The solvent mixture used comprises a solution of 20% by weight diethanolamine, 20% by weight diethylene glycol and 60% by weight N-methyl-ε-caprolactam.

The stress-relief gas of the first stage is redensified at a pressure of 90 at. and admixed with the crude gas, prior to entering the absorber. The stress-relief gas of the second stage at 5 at. is used as heating gas.

The regeneration of the solvent is effected in a solid filler-containing column at 1.1 at. and at 150° C. 100 m³/h of the purified natural gas is used as strip gas. The purified gas has the following composition, compared to the crude gas:

|  | Crude Gas Vol.% | Pure Gas Vol.% |
|---|---|---|
| $CH_4$ | 90 | 95.6 |
| $C_2H_6$ | 3 | 3.15 |
| $C_3H_8$ | 1 | 0.9 |
| $C_4H_{10}$ | 0.5 | 0.35 |
| $CO_2$ | 5 | 50 ppm |
| $N_2S$ | 0.5 | 5 ppm |
| $CH_3$—SH | 300 ppm | 12 ppm |
| $CH_3$—$CH_2$—SH | 100 ppm | 8 ppm |
| $CH_3$—S—$CH_3$ | 100 ppm | 10 ppm |

EXAMPLE 3

From 10,000 m³/h natural gas, organic sulphur is to be removed to <30 ppm. At the same time, the gas is to be dried to a dew point of <−20° C. Furthermore, a fraction is to be extracted from the natural gas which has a concentration of propane and butane, and from which liquid gas can be produced by conventional methods. The crude gas has a composition which coincides with the composition of the gas in Example 1. The solvent used is a mixture of 40% by weight diethyleneglycol and 60% by weight N-methyl-ε-caprolactam. At a pressure of 50 at., the gas is charged into a plate column composed of 25 plates with 15 m³/h solvent at 20° C. The purified gas has the following composition:

| $CH_4$ | 93.05 | Vol.% |
|---|---|---|
| $C_2H_6$ | 4.67 | " |
| $C_3H_8$ | 1.70 | " |
| $C_4H_{10}$ | 0.50 | " |
| $C_5H_{12}$ | 0.10 | " |
| $C_6H_{14}$ |  |  |

| | -continued | |
|---|---|---|
| $C_7H_{16}$ | 200 | ppm |
| $CH_3-CH_2-SH$ | 5 | ppm |
| $CH_3-S-CH_3$ | 10 | ppm |
| $CH_3-SH$ | 15 | ppm |

Vapor dew point $-20°$ C

The regeneration of the charged solvent is effected in a plurality of stages. In the first separation stage, at 20 kp/cm², primarily the $CH_4$ is removed. This is used as strip gas by adding pure gas. In the second separation stage, 200 m³/h i.N. gas is removed. The last stage of the regeneration of the solvent is effected in a strip column, at 160° C.

The separated gas of the second stage has the following composition:

| | | |
|---|---|---|
| $CH_4$ | 43.6 | Vol.% |
| $C_2H_6$ | 23.7 | " |
| $C_3H_8$ | 22.5 | " |
| $C_4H_{10}$ | 9.0 | " |

Although the invention has been described with reference to specific examples, it will be apparent to one skilled in the art that various modifications may be made thereto which fall within its scope.

We claim:

1. A method of processing natural or synthetic gases containing water vapor, acidic and neutral sulphur compounds and higher hydrocarbons, which compises treating said gas with an anhydrous solvent containing N-methyl-ε-caprolactam, an alkanolamine and a glycol to simultaneously remove said sulphur compounds; hydrocarbons and water vapor.

2. The method as in claim 1, wherein the glycol content constitutes about 5% to 60% by weight, and the alkanolamine content constitutes about 0 to 30% by weight.

3. The method as in claim 1, wherein the glycol is selected from the class consisting of di-ethylene glycol and tri-ethylene glycol.

4. A method in accordance with claim 1, wherein said anhydrous solvent is substantially completely regenerated for reuse in the processing of natural and synthetic gases.

5. A method as in claim 1, wherein the N-methyl-ε-caprolactam constitutes the major constituent of the solvent.

6. A method in accordance with claim 5, wherein the N-methyl-ε-caprolactam constitutes about 60% to 90% by weight.

* * * * *